United States Patent
Howland

(10) Patent No.: US 6,234,981 B1
(45) Date of Patent: May 22, 2001

(54) VAPOR DEPOSITION COATED INTRACORPOREAL DEVICE

(75) Inventor: Jonathan M. Howland, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/223,224

(22) Filed: Dec. 30, 1998

(51) Int. Cl.⁷ .................................................. A61B 5/00
(52) U.S. Cl. ............................................................ 600/585
(58) Field of Search ................................. 600/585, 433, 600/434; 604/95, 96, 280, 281

(56) References Cited

U.S. PATENT DOCUMENTS

| | | | |
|---|---|---|---|
| 4,538,622 | 9/1985 | Sanson et al. | 128/772 |
| 4,748,986 | 6/1988 | Morrison et al. | 128/772 |
| 4,917,104 | 4/1990 | Rebell | 128/772 |
| 4,925,445 | 5/1990 | Sakamoto et al. | 604/95 |
| 5,069,217 | 12/1991 | Fleischhaker, Jr. | 128/657 |
| 5,069,226 | 12/1991 | Yamauchi et al. | 128/772 |
| 5,135,503 | 8/1992 | Abrams | 604/164 |
| 5,141,487 * | 8/1992 | Liprie | 600/585 |
| 5,171,383 | 12/1992 | Sagaye et al. | 148/564 |
| 5,188,621 * | 2/1993 | Samson | 600/585 |
| 5,213,111 | 5/1993 | Cook et al. | 128/772 |
| 5,230,348 | 7/1993 | Ishibe et al. | 128/772 |
| 5,238,004 | 8/1993 | Sahatjian et al. | 128/772 |
| 5,253,653 | 10/1993 | Daigle et al. | 128/772 |
| 5,341,818 | 8/1994 | Abrams et al. | 128/772 |
| 5,345,945 | 9/1994 | Hodgson et al. | 128/772 |
| 5,409,015 | 4/1995 | Palermo | 128/772 |
| 5,506,059 | 4/1996 | Robbins et al. | 428/457 |
| 5,520,194 | 5/1996 | Miyata et al. | 128/772 |
| 5,588,443 | 12/1996 | Davidson | 128/772 |
| 5,607,463 | 3/1997 | Schwartz et al. | 623/1 |
| 5,628,787 | 5/1997 | Mayer | 623/1 |
| 5,630,840 | 5/1997 | Mayer | 623/1 |
| 5,636,641 | 6/1997 | Fariabi | 128/772 |
| 5,637,089 | 6/1997 | Abrams et al. | 604/95 |
| 5,647,858 | 7/1997 | Davidson | 604/264 |
| 5,664,580 | 9/1997 | Erickson et al. | 128/772 |
| 5,666,968 * | 9/1997 | Imran et al. | 600/585 |
| 5,695,111 | 12/1997 | Nanis et al. | 228/206 |
| 5,701,911 * | 12/1997 | Sasamine et al. | 600/585 |

(List continued on next page.)

FOREIGN PATENT DOCUMENTS

| | | |
|---|---|---|
| 0515078 | 11/1992 | (EP) . |
| 0652026 | 5/1995 | (EP) . |
| 0515078 | 12/1997 | (EP) . |
| 0838330 | 4/1998 | (EP) . |

OTHER PUBLICATIONS

International Searching Authority communication, "International Search Report" dated Mar. 3, 2000.

Primary Examiner—Cary O'Connor
Assistant Examiner—Pamela L. Wingood
(74) Attorney, Agent, or Firm—Heller, Ehrman, White & McAuliffe LLP

(57) ABSTRACT

A method of joining two members of a medical device wherein at least one of the members has a thin layer of joinable material deposited on the surface thereof by vapor deposition, preferably, physical vapor deposition. A guidewire for advancement of intraluminal medical devices may be manufactured by depositing a thin layer of joinable material on the surface of a component which is made from a reactive alloy with a tenacious oxide layer. The thin layer of joinable material facilitates joining difficult to bond materials with other components of the guidewire. Physical vapor deposition may also be used to treat components of medical devices, such as distal guidewire segments, in order to alter their mechanical properties. Specifically, a pseudoelastic alloy segment may be made shapeable by vapor deposition of a non-pseudoelastic metal thereon.

21 Claims, 2 Drawing Sheets

U.S. PATENT DOCUMENTS

| | | | |
|---|---|---|---|
| 5,720,300 | 2/1998 | Fagan et al. | 128/772 |
| 5,725,570 | 3/1998 | Heath | 623/1 |
| 5,725,572 | 3/1998 | Lam et al. | 623/1 |
| 5,733,326 | 3/1998 | Tomonto et al. | 623/1 |
| 5,824,056 | 10/1998 | Rosenberg | 623/1 |
| 5,824,077 | 10/1998 | Mayer | 623/11 |
| 5,843,166 | 12/1998 | Lentz et al. | 623/1 |
| 5,891,191 | 4/1999 | Stinson | 623/1 |

* cited by examiner

VAPOR DEPOSITION COATED INTRACORPOREAL DEVICE

BACKGROUND OF THE INVENTION

This invention relates to joining elongated members such as elements of guidewires for advancing intraluminal devices within body lumens. Conventional guidewires for stent delivery catheters, balloon dilatation catheters, atherectomy catheters and the like usually comprise an elongated core member with one or more tapered sections near the distal end thereof and a flexible body such as a helical coil disposed about the distal portion of the core member. A shapeable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system. In some cases, the physician will bend the distal end of the core member to facilitate advancement of, the guidewire through the turns of the patient's body lumen, necessitating the shapeable member.

In a typical coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated. A desired diagnostic or therapeutic system can then be advanced over the guidewire to perform a procedure at the site of the lesion. Typical procedures include balloon angioplasty and intracoronary stent delivery.

A major requirement for guidewires is that they have sufficient column strength to be pushed through a patient's vascular system or other body lumen without kinking. However, the distal portion must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,636,641 (Fariabi); and U.S. Pat. No. 5,345,945 (Hodgson, et al.) which are hereby incorporated herein in their entirety by reference thereto.

One approach to achieving both flexibility and column strength in a guidewire is to use a pseudoelastic alloy for a core member, such as NiTi. When stress is applied to a core member exhibiting pseudoelastic characteristics at a temperature at or above which the transformation of martensite phase to the austenite phase is complete, the core member deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress is necessary to cause further deformation.

If the load on the pseudoelastic alloy is removed before any permanent deformation has occurred, the martensitic core metal will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction.

This ability to incur significant strain at relatively constant stress upon the application of a load and to recover from the deformation upon the removal of the load is commonly referred to as pseudoelasticity. These properties to a large degree allow a guidewire core of a pseudoelastic material to have both flexibility and strength. However, many pseudoelastic alloys, particularly titanium containing alloys, are difficult to join or secure to other components, primarily because a tenacious oxide layer that develops on the surface of such alloys. Prior methods for attaching subassemblies to psuedoelastic or superelastic components included molten or fusion salt etching and then pre-tinning with gold or similar materials to facilitate forming a strong bond, as seen in U.S. Pat. No. 5,695,111 to Nanis, et al. which is hereby incorporated in its entirety. In addition, it is often desirable for a guidewire to have an integral core member of a unitary piece of metal that extends from a proximal section to the distal tip of the guidewire. However, it also often desirable for the distal tip of a guidewire to be shapeable with manual deformation so that a physician can tailor the shape of the distal tip to the vasculature that must be traversed. As discussed above, pseudoelastic alloys can withstand a large amount of stress without incurring plastic deformation, and are thus difficult to shape when used as core members in distal guidewire sections.

What has been needed and heretofore unavailable, however, is a method for manufacturing a guidewire with a superelastic or pseudoelastic component which will allow the component to accept a weld, solder or adhesive joint with ease of manufacture and low cost. What has also been needed is a distally contiguous distal segment of a guidewire core made of a pseudoelastic or superelastic alloy which can be shaped or bent to allow for guiding, without the need of a separate non-pseudoelastic piece, i.e. a stainless steel shaping ribbon.

SUMMARY OF THE INVENTION

The present invention is directed to a method for joining a first member of a medical device to a second member of a medical device by depositing a thin layer of joinable material on at least a portion of the first member by vapor deposition, preferably, by physical vapor deposition. The thin layer of joinable material can then be secured by suitable methods to the second member of the medical device with a joining agent or joining process. The invention is also directed to a medical device, preferably a guidewire, that has at least two members or elements joined by using a thin layer of joinable material deposited by vapor deposition.

A guidewire having features of the invention preferably has at least one elongate core section that is made of a pseudoelastic alloy that is secured or bonded to other elongate core sections, flexible body members or the like. Preferably, NiTi alloy is used for the pseudoelastic alloy material, however, other suitable pseudoelastic alloys may be used. The joining or securing of pseudoelastic components, particularly titanium containing alloys, in a medical device is often complicated by a tenacious oxide layer that forms on the surface of such a pseudoelastic alloy which does not readily accept joining agents such as molten material of the same pseudoelastic alloy during welding, solder or polymer adhesives such as heat curable epoxies or cyanoacrylates. The present invention solves this problem by using vapor deposition to coat the pseudoelastic alloy with a readily joinable material such as metals like stainless steel, suitable polymers or the like. The joinable material layer creates a bondable or joinable surface that can be welded, soldered or bonded. Suitable joinable materials can include stainless steel, gold, platinum, tantalum or any other suitable material that lends itself to bonding, welding or soldering. Suitable joining agents include molten metals of the same composition as the joinable material, various solders, various brazes, or polymer adhesives such as heat curable epoxies, cyanoacrylates and the like.

One embodiment of the invention is directed to the use of vapor deposition to apply a thin layer of joinable material to a tapered distal NiTi core used in guidewires. The layer can be specifically deposited in areas to which other subassemblies must be attached using a solder joint or other suitable means. The vapor deposition of a joinable material allows the subassemblies to attach to the distal core.

In another aspect of the invention, vapor deposition is used to process a distal segment of a pseudoelastic distal section of a guidewire core member so as to create a distally contiguous shapeable member. The shapeable member functions similarly to a separate stainless steel shaping ribbon but is integral to the distal section so as to minimize any risk of detachment or failure of a bond therebetween. It has been found that by subjecting the distal segment of a distal section of an elongate core member made of pseudoelastic alloy to vapor deposition of stainless steel or other non-pseudoelastic metals, that the distal segment of pseudoelastic alloy can be made shapeable with similar mechanical properties to a stainless steel shaping ribbon. Shapeability of a superelastic or psuedoelastic distal segment of a guidewire is achieved by vapor depositing sufficient stainless steel or other suitable metal or material onto the distal segment so as to decrease the pseudoelastic characteristics of the distal segment as a whole.

These and other advantages of the invention will become more apparent from the following detailed description of the invention when taken in conjunction with the accompanying exemplary drawings.

DETAILED DESCRIPTION

Figure 1:
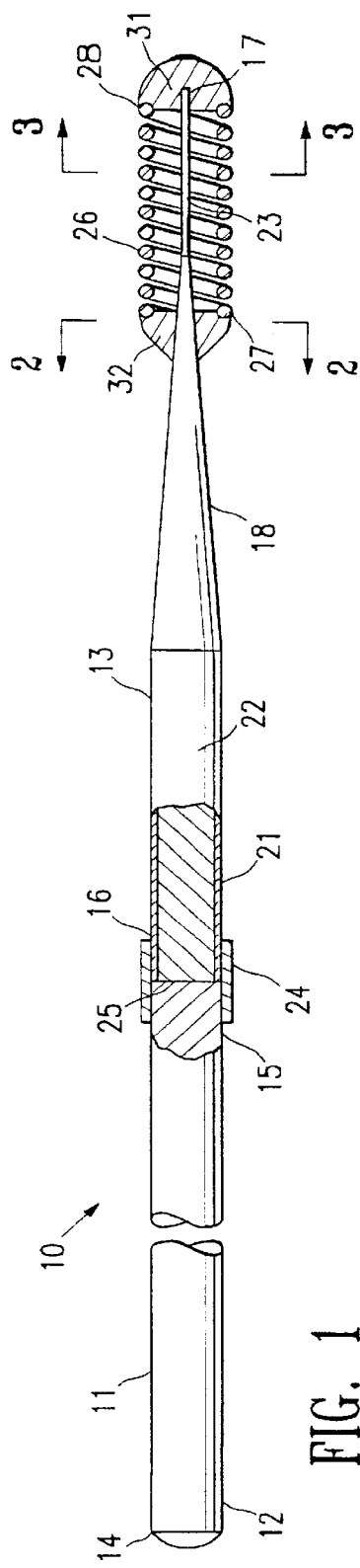
FIG. 1 shows an elevational view in partial section of an embodiment of a guidewire having features of the invention.

FIG. 1 shows an elevational view in partial section of a guidewire 10 having features of the invention. The guidewire 10 has an elongate core 11 with a proximal section 12 and a distal section 13. The proximal section 12 has a proximal end 14 and a distal end 15. The distal section 13 has a proximal end 16 and a distal end 17. The proximal section 12 is made from a high strength material, preferably stainless steel, and is preferably round in cross section. The proximal section 12 is shown as a constant diameter section but may have one or more tapered segments thereon. The diameter of the proximal section 12 can be from about 0.010 inches to about 0.025 inches, but is preferably about 0.012 to about 0.016 inches. The length of the proximal section 12 can be from about 75 to about 300 cm, but is preferably about 125 cm to about 175 cm.

The distal section 13 has a tapered segment 18. Although the embodiment shown in FIG. 1 has only one tapered segment 18 on the distal section, any number of tapered segments can be used as the performance requirements of the guidewire 10 dictate. The tapered segment 18 creates a more flexible distal section for improved trackability. The distal section 13 is made from a pseudoelastic alloy, such as NiTi, and has a thin layer of joinable material 21 vapor deposited thereon. Preferably, any tenacious oxide layer disposed on the distal section 13, such as titanium oxide, has been removed from an outer surface 22 of the distal section prior to the application of the thin layer of joinable material 21 in at least those areas of the outer surface on which the joinable material is disposed. The oxide layer can be removed by chemical or plasma etching or other suitable means. The entire outer surface 22 of the distal section may be coated with a thin layer of joinable material 21, or only desired portions thereof. For example, the distal section can be coated with the thin layer of joinable material 21 only in areas of the outer surface 22 where other components of the guidewire will be attached. Preferably about 15 to about 20 cm of the distal end 17 and proximal end 16 of the distal section 13 have a thin layer of joinable material 21 deposited thereon. The thin layer of joinable material 21 is preferably applied with a vapor deposition process which produces a thin layer having a thickness up to about 20 microns, preferably about 1 to about 5 microns, and more preferably about 1 to about 3 microns.

The distal section 13 has a distal segment 23 at the distal end 17 which is a segment having a small cross section which provides flexibility and preferably shapeability to the distal end 17. The distal segment 23 is a distally contiguous and integral portion of the distal section 13 and is made of the same pseudoelastic alloy as the rest of the distal section. It is desirable for the distal segment 23 to have shapeable characteristics by virtue of the deposition of the thin layer of joinable material 21. The thin layer of joinable material can be made of metals such as stainless steel, which can have non-pseudoelastic mechanical properties which give malleable properties and shapeability to the distal segment. The thickness of the thin layer of joinable material 21 on the distal segment 23 required to give the distal segment shapeable properties can vary depending on the material used for the distal section and the processing undergone by that material. The thickness of the thin layer of joinable material 21 required for a shapeable distal segment 23 can also depend on the type of material used for the thin layer. If stainless steel is used for the thin layer 21 on a distal segment 23 of NiTi alloy, the thickness of the thin layer required for a shapeable distal segment is about 1 to about 2 microns, although a thickness greater than 2 microns can give greater shapeability.

By way of example, a preferred embodiment of a distal section 13, having a shapeable distal segment 23 is produced by starting with a piece of NiTi alloy wire approximately 0.0135 inches in diameter and about 40 to about 45 cm in length. A distal taper is ground by conventional centerless grinding techniques onto the distal section 13 to reduce the nominal 0.0135 inch diameter to a diameter of about 0.0025 to about 0.0035 inches at the distal segment 23. The distal segment 23 at this stage will have a substantially constant outer diameter and a length of about 3 to about 10 mm, preferably about 5 to about 8 mm. The distal section 13 is then chemically etched, preferably in a mixture of nitric acid and sulfuric acid, to remove the oxide layer on the distal section. About 16 to about 20 cm of the distal end of the distal section 13 is then inserted into a suitable PVD chamber and plasma etched for about 5 minutes in a working gas such as argon. The temperature within the PVD chamber during the plasma etch is about 200 to about 300 degrees Centigrade. After plasma etching, the portion of the distal section 13 within the PVD chamber is PVD coated with a layer of 316 stainless steel to a thickness of about 1 to about 2 micrometers. The PVD coating process normally takes about 5 to about 10 minutes to complete. The temperature within the PVD coating chamber during PVD coating of the 316 stainless steel is about 200 to about 300 degrees Centigrade. After the PVD coating process is complete, the distal section 13 is removed from the PVD coating chamber and the distal segment 23 is flattened in a pneumatic press to a thickness of about 0.0015 to about 0.002 inches. In this flattened state, with a 1 to 2 micrometer thick layer of stainless steel applied, the distal segment 23 will exhibit shapeable characteristics.

The proximal end 16 of the distal section 13 and distal end 15 of the proximal section 12 are joined with a sleeve 24. The sleeve 24 is disposed over at least a portion of the proximal end 16 of the distal section 13 and the distal end 15 of the proximal section 12. The sleeve 24 can be attached in a variety of ways, but is preferably soldered to the distal end 15 of the proximal section and the thin layer of joinable material 21 disposed on the proximal end 16 of the distal section at a joining interface 25. The sleeve 24 can be made from a variety of high strength materials, but is preferably made from a tube of stainless steel. In such an embodiment, joinable material 21 is also stainless steel.

A flexible body member 26 is disposed about the distal section 13. The flexible body 26 has a proximal end 27 and a distal end 28 and is preferably made of a helical coil of metal. The flexible body 26 preferably has an outer diameter similar to that of the proximal section 12 of the elongate core 11. The flexible body 26 can be from about 1 to about 50 cm in length, preferably about 5 to about 20 cm in length, and more preferably about 7 to about 12 cm. The flexible body 26 can be constructed from radiopaque metals such as gold, platinum, tantalum or the like, but may also be made from non-radiopaque metals such as stainless steel. Combinations of radiopaque and non-radiopaque metals can also be used for the flexible body 26, such as stainless steel with a gold or platinum outer layer. The material from which the flexible body 26 is made generally has a transverse diameter of about 0.001 to about 0.004 inch, preferably about 0.002 to about 0.003 inch (0.05 mm). Multiple turns of the distal portion of flexible body may be expanded to provide additional flexibility. The flexible body may 26 have transverse dimensions about the same as the proximal core section.

The flexible body 26 may also consist of a polymer or composite jacket of polyimide, polyethylene, polyurethane, TFE, PTFE, ePTFE and the like. If a polymer material is used for the flexible body 26, it may be desirable to use a similar polymer for the thin layer of joinable material 21 disposed on the distal section 13.

The distal end 28 of the flexible body 26 is secured to the distal end 17 of the distal section 13 of the elongate core 11 by a first solder body 31. The first body of solder 31 may be formed into a rounded shape to create a non-traumatic configuration for the distal end 17 of the distal section. The proximal end 27 of the flexible body 26 is secured to the distal section 13 by a second solder body 32. The flexible body 26 may be secured to the distal section 13 along its length in other locations between the distal end 28 and proximal end 27. The flexible body 26 may also be constructed of several different lengths of helical coil which may be made from different or similar materials. For example, the flexible body 26 may be made from two helical coils, one of which is radiopaque, the other of which is non-radiopaque.

The first solder body 31 and second solder body 32 are disposed between the respective portions of the flexible body 26 and the distal section 13 of the elongate core 11. The solder bodies are preferably made of a material that adheres readily to both the material of the flexible body 26 and that of the thin layer of joinable material 21 disposed on the distal section 13. Preferably both the flexible body 26 and the thin layer of joinable material 21 are made of stainless steel.

Figure 2:
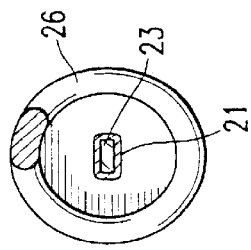
FIG. 2 shows a transverse cross sectional view of the guidewire of FIG. 1 taken at 2—2.

FIG. 2 is a transverse cross sectional view of the guidewire 10 of FIG. 1. The second solder body 32 is disposed about and bonded to the thin layer of joinable material 21. The thin layer of joinable material 21 is disposed about the distal section 13 of the elongate core 11.

Figure 3:
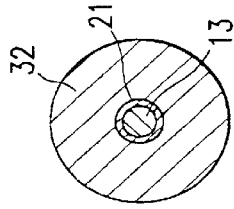
FIG. 3 shows a transverse cross sectional view of the guidewire of FIG. 1 taken at 3—3.

FIG. 3 is a transverse cross sectional view of the guidewire 10 of FIG. 1. The flexible body 26 is disposed about the distal segment 23 of the distal section 13 of the elongate core 11. The thin joinable layer 21 is disposed about the distal segment 23. The distal segment 23 has a flattened rectangular cross section, but may also have a round, elliptical or square cross sectional shape or any other suitable configuration. A flattened distal segment 23 improves the shapeability of the segment.

Figure 4:
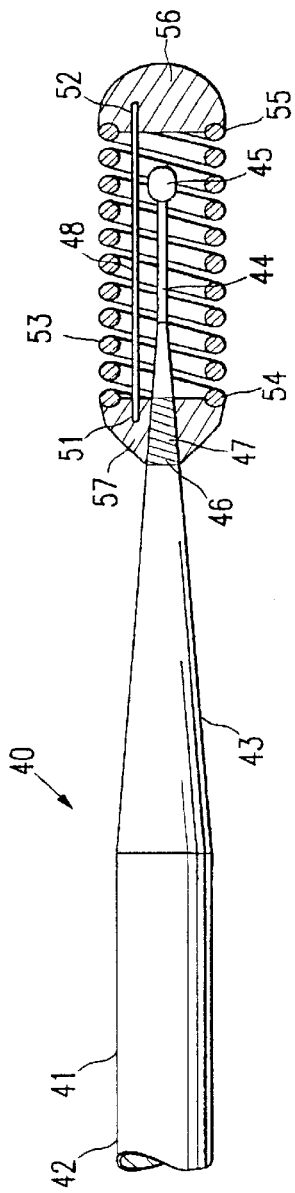
FIG. 4 shows an elevational view of an embodiment of a guidewire having features of the invention.

FIG. 4 depicts an alternative embodiment of a guidewire 40 having features of the invention. A distal section 41 of an elongate core 42 has a tapered segment 43, a distal segment 44 and a distal end 45. The distal section 41 can be made from materials similar to those described for the distal section of the guidewire of FIG. 1, and can be similarly attached to a proximal section. The distal section 41 is preferably made from NiTi alloy which has been coated with a thin layer of joinable material 46 on a bonding area 47. In the embodiment shown in FIG. 4, only the portions of the distal section 41 which are to be bonded to other components, i.e. the bonding area 47, have been coated with a thin layer of joinable material 46 such as stainless steel.

A shaping ribbon 48 having a proximal end 51 and a distal end 52 is disposed adjacent the distal segment 44. The shaping ribbon 48 can be made from any suitable high strength material, but is preferably made from a flattened piece of stainless steel. A flexible body 53 having a proximal end 54 and a distal end 55 is disposed about at least a portion of the distal segment 44 and the shaping ribbon 48. The distal end 55 of the flexible body 53 is secured to the distal end 52 of the shaping ribbon 48 with a first body of solder 56. The proximal end 54 of the flexible body 53 is secured to the proximal end 51 of the shaping ribbon 48 and the bondable area 47 of the distal section 41 with a second body of solder 57. The distal end 45 of the distal section 41 is disposed within the flexible body 53. The flexible body 53 may be constructed in a manner similar to the flexible body 26 of the embodiment of FIG. 1.

Figure 5:
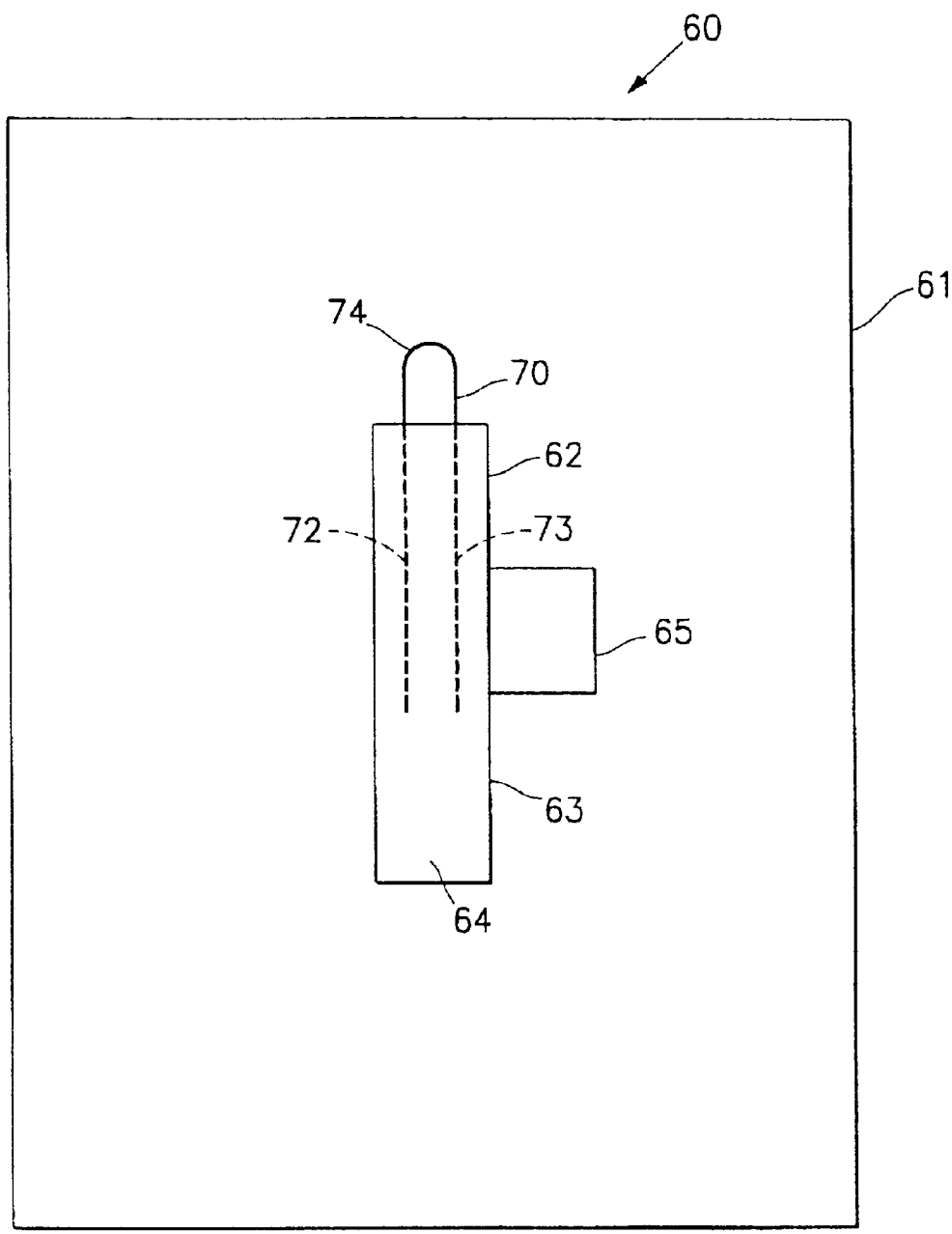
FIG. 5 is a schematic view of a device which can be used for vapor deposition processing with a distal section of a guidewire core positioned within a vapor deposition chamber.

FIG. 5 depicts a schematic view of a vapor deposition apparatus 60. The apparatus 60 has a vacuum chamber 61 disposed about a vapor deposition device 62. The vapor deposition device 62 preferably has an elongate hollow body 63 with a vapor deposition chamber 64 and a sputtering device 65 operably attached thereto. A distal section 70 of a guidewire having features of the invention is shown with a proximal end 72 and a distal end 73 disposed within the vapor deposition chamber 64. In this way, the proximal end 72 and distal end 73 of the distal section 70 can be coated with a thin layer of joinable material without coating an intermediate portion 74 of the distal section 70.

The vapor deposition process may be carried out by evaporative or sputtering techniques. Preferably, the vapor deposition process is physical vapor deposition utilizing a sputtering technique. Argon is typically use as a working gas, which forms a plasma in the vacuum. After cleaning the NiTi of oxide, the argon plasma acts as an energizing agent to impinge upon the molecules of the target material. The target material is made of a joinable material that is to be formed in a thin layer on the desired segment of the core wire. Once energized by the argon gas molecules, the energized target material molecules leave the target substrate and attach to the core material substrate. The energized target material molecules can be compelled toward the core section material during the deposition process by applying a voltage potential between the target material and the core section substrate to be coated. The vapor deposition process described above can be carried out with the distal core section held in a stationary position, however, the process may also be carried out with a continuous dynamic process wherein a long piece of distal core section material is continuously drawn through the vapor deposition chamber with the chamber activated thereby coating or applying a thin layer of joinable material to the entire length of the distal section or to multiple distal sections which can be attached end to end for vapor deposition processing and separated later.

The vapor deposition process normally involves inserting a shaped or tapered NiTi core wire into a vapor deposition vacuum chamber, in its entirety, or any portion or portions thereof. Preferably, about 15 to about 20 cm of the distal end and about 15 to about 20 cm of the proximal end of a pseudoelastic distal core section is disposed within the vapor deposition chamber. The vapor deposition chamber dimensions can be about 30 inches in length with an 18 inch diameter, although those skilled in the art will realize that a wide variety of chamber dimensions can be used. The vapor deposition chamber is located within a larger vacuum chamber which surrounds the vapor deposition chamber. The vacuum chamber is pumped down to a pressure of about 5.0E-6 Torr. Argon is injected into the vacuum chamber to a pressure of about 3.0 mTorr. The argon can then optionally be energized into a plasma for the purpose of precleaning the portions of the NiTi core segment disposed within the vapor deposition chamber. The precleaning process can be designed to remove the tenacious oxide layer on the outside surface of the distal guidewire core section.

The target material or joinable material which is deposited on the distal core section by the vapor deposition processing can be a relatively unreactive metal or alloy such as platinum, gold, silver or stainless steel or the like. Stainless steel is preferred because it is inexpensive compared to the other mentioned materials and the proximal section of the elongate core is typically constructed of stainless steel which facilitates soldering or bonding of like materials. The longer the vapor deposition process is operated for any given core section or other substrate to which a thin layer of joinable material is deposited, the thicker the deposited coating will be. The thin layer of joinable material can be applied at a thickness up to 100 microns, but is preferably applied at a thickness up to 2 microns. More preferably, the coating will have a thickness of about 1 to about 2 microns, which is sufficient for a high integrity solder joint.

The entire vapor deposition process is preferably temperature controlled in order to avoid altering the mechanical or pseudoelastic properties of the distal core section or of any other material that is be treated by the vapor deposition process. The vapor deposition processing can be performed at a temperature up to about 300° C., but is preferably performed at a temperature of about 200° C. or lower. This vapor deposition process can be used to deposit any suitable material on any similar or dissimilar material that requires a surface interface or thin layer that would facilitate joining.

The invention has been described herein in terms of a vapor deposition, preferably a physical vapor deposition process for joining material. Those skilled in the art will recognize that other forms of deposition may be employed. Moreover, while particular forms of the invention have been illustrated and described, it will be apparent that various modifications can be made without departing from the spirit and scope of the invention. Accordingly, it is not intended that the invention be limited, except as by the appended claims.

What is claimed is:

1. A medical device comprising:
    a) a first member;
    b) a second member;
    c) a thin layer of joinable material up to about 5 microns in thickness on at least one of the members; and
    d) a joining material disposed upon the thin layer of joinable material joining the first member and the second member.

2. The medical device of claim 1 wherein the first member is made of the same metal as the second member.

3. The medical device of claim 1, wherein the first member is a different metal than the second member.

4. The medical device of claim 1, wherein the first member is a different metal from the second member that will not facilitate a strong solder joint together to the metal forming the second member.

5. The medical device of claim 1, wherein the thin layer of joinable material is a metal.

6. The medical device of claim 1, wherein the thin layer of joinable material is a non-metal.

7. The medical device of claim 1, wherein the thin layer of joinable material is up to about 2 microns in thickness.

8. The medical device of claim 1, wherein the thin layer of joinable material is between about 1 and 2 microns thick.

9. A guidewire for intraluminal advancement of a medical device within a patient, comprising:

a) a proximal section of an elongate core with a proximal end and a distal end;

b) a distal section of the elongate core with at least one tapered section, a proximal ends a distal end and a thin layer of joinable material on at least a portion of the distal section with the distal end of the proximal section secured to the proximal end of the distal section by a joining agent; and c) a flexible body having a proximal end and a distal end disposed about and secured to at least a portion of the distal section with a joining agent.

10. The guidewire of claim 9, further comprising a distal segment at the distal end of the distal section of the elongate core.

11. The guidewire of claim 10 wherein the distal section is comprised of a pseudoelastic alloy and the distal segment of the distal section has a sufficient layer of non-pseudoelastic metal on it to make it shapeable.

12. The guidewire of claim 9, wherein a distal segment of the distal section is flattened.

13. The guidewire of claim 9, wherein the joinable material deposited is gold.

14. The guidewire of claim 9, wherein the joinable material deposited is an alloy.

15. The guidewire of claim 9, wherein the alloy is stainless steel.

16. The guidewire of claim 9, wherein the joinable material deposited is a polymer.

17. The guidewire of claim 9, wherein the distal section is completely covered with the deposited joinable material.

18. The guidewire of claim 9, wherein the joinable material is only deposited on the distal section in areas to which other members are joined.

19. The guidewire of claim 9, wherein the thickness of the thin layer is up to 2 microns.

20. The guidewire of claim 9, wherein the thickness of the thin layer is between 1 and 2 microns.

21. The guidewire of claim 9, wherein the thin coating of joinable material is sufficient to create a shapeable distal segment of the distal section.

* * * * *

UNITED STATES PATENT AND TRADEMARK OFFICE
CERTIFICATE OF CORRECTION

PATENT NO. : 6,234,981 B1
DATED : May 22, 2001
INVENTOR(S) : Jonathan M. Howland It is certified that error appears in the above-identified patent and that said Letters Patent is hereby corrected as shown below:

Column 9,
Line 4, change "ends", to read -- end, --.

Column 10,
Line 3, change "9", to read -- 14 --.

Signed and Sealed this

Twenty-seventh Day of August, 2002

*Attest:*

*Attesting Officer*

JAMES E. ROGAN
*Director of the United States Patent and Trademark Office*